(12) United States Patent
Elmasry

(10) Patent No.: US 10,315,381 B2
(45) Date of Patent: Jun. 11, 2019

(54) THREE LAYER TEST TUBE AND ASSOCIATED METHODS

(71) Applicant: Medhat N. Elmasry, Hillsville, VA (US)

(72) Inventor: Medhat N. Elmasry, Hillsville, VA (US)

( * ) Notice: Subject to any disclaimer, the term of this patent is extended or adjusted under 35 U.S.C. 154(b) by 0 days.

(21) Appl. No.: 15/378,543

(22) Filed: Dec. 14, 2016

(65) Prior Publication Data
US 2017/0274373 A1 Sep. 28, 2017

Related U.S. Application Data

(60) Provisional application No. 62/313,444, filed on Mar. 25, 2016.

(51) Int. Cl.
*B01L 3/14* (2006.01)
*B32B 1/02* (2006.01)
(Continued)

(52) U.S. Cl.
CPC .................. *B32B 5/18* (2013.01); *B01L 7/00* (2013.01); *B01L 9/06* (2013.01); *B32B 1/02* (2013.01); *B32B 3/08* (2013.01); *B32B 5/24* (2013.01); *B32B 21/02* (2013.01); *B32B 21/04* (2013.01); *B32B 27/06* (2013.01); *B32B 27/302* (2013.01); *B32B 27/40* (2013.01); *B32B 27/42* (2013.01); *B32B 29/002* (2013.01); *G01N 1/42* (2013.01); *B01L 2300/0832* (2013.01); *B01L 2300/0887* (2013.01); *B01L 2300/1877* (2013.01); *B01L 2400/0683* (2013.01); *B32B 2250/03* (2013.01); *B32B 2255/102* (2013.01); *B32B 2262/062* (2013.01); *B32B 2262/101* (2013.01);
(Continued)

(58) Field of Classification Search
CPC ............ B01L 3/14; B01L 3/00; B01L 3/5082; B01L 3/508; B01L 3/50; B32B 1/02; B32B 1/00; B32B 5/18; B32B 5/00
USPC .................................. 422/913, 914; 436/174
See application file for complete search history.

(56) References Cited

U.S. PATENT DOCUMENTS 3,378,333 A * 4/1968 Brite .................... A61M 11/041
126/263.05
6,133,041 A * 10/2000 Park .................... G01N 33/0044
422/80

(Continued)

OTHER PUBLICATIONS

"All About Blood." Red on Tap. Genensis Framework, May 9, 2011. Web. Nov. 20, 2015.

(Continued)

*Primary Examiner* — Christine T Mui
(74) *Attorney, Agent, or Firm* — Ben Schroeder Law, PLLC

(57) ABSTRACT

A two layer and/or a three-layer device is disclosed that allows samples therein to remain at a warmer or a colder temperature than would be ordinarily possible without the use of the two or three-layer device. The two-layer device contains an interior layer that comprises the sample, and a middle or intermediate layer that comprises chemical species that undergoes an exothermic or endothermic reaction. The three layer device further has an outer layer that contains an insulating layer. When the three layer device is used for samples, the temperature of the sample can remain at a temperature around 11° C. or less for at least about 5.5 to 6 hours.

22 Claims, 13 Drawing Sheets

(51) Int. Cl.
- *B32B 5/18* (2006.01)
- *B01L 7/00* (2006.01)
- *B01L 9/06* (2006.01)
- *B32B 5/24* (2006.01)
- *B32B 21/02* (2006.01)
- *B32B 21/04* (2006.01)
- *B32B 27/06* (2006.01)
- *B32B 27/30* (2006.01)
- *B32B 27/40* (2006.01)
- *B32B 27/42* (2006.01)
- *B32B 29/00* (2006.01)
- *B32B 3/08* (2006.01)
- *G01N 1/42* (2006.01)
- *B01L 3/00* (2006.01)
- *G01N 33/49* (2006.01)

(52) U.S. Cl.
CPC ... *B32B 2262/108* (2013.01); *B32B 2266/025* (2013.01); *B32B 2266/0228* (2013.01); *B32B 2266/0285* (2013.01); *B32B 2266/049* (2016.11); *B32B 2266/126* (2016.11); *B32B 2307/304* (2013.01); *B32B 2439/02* (2013.01); *G01N 33/49* (2013.01)

(56) References Cited

U.S. PATENT DOCUMENTS

| | | | |
|---|---|---|---|
| 6,289,889 B1* | 9/2001 | Bell | A61F 7/03 126/263.07 |
| 7,047,832 B1* | 5/2006 | von Meyer | G01L 7/18 422/106 |
| 2014/0105808 A1* | 4/2014 | McNeel | C01B 21/091 423/413 |

OTHER PUBLICATIONS

Cuhadar et al. Stability Studies . . . , Biochemia Medica. Croatian Society of MedicalBiochemistry and Laboratory Medicine. Web. Dec. 11, 2015.
"LabNotes—vol. 14." Managing Preanalytical Variability in Hematology. Becton, Dickinson and Company. 2014 BD, Nov. 10, 2004. Web. Nov. 30, 2015.
"Result Filters." National Center for Biotechnology Information. U.S. National Library of Medicine. Web. Dec. 11, 2015.
Trulock, E.P., and Iii. Arterial Blood Gases. U.S National Library of Medicine, Jan. 17, 1990. Web. Nov. 30, 2015.

* cited by examiner

THREE LAYER TEST TUBE AND ASSOCIATED METHODS

This application claims priority under 35 USC 119(e) to U.S. Provisional Application No. 62/313,444 filed Mar. 25, 2016, the entire contents of which are incorporated by reference in its entirety.

FIELD OF THE INVENTION

This invention relates to a three-layer test tube that allows samples therein to remain at a colder temperature than would be ordinarily possible without the use of the three-layer test tube. The three-layer tube comprises an interior layer that comprises the sample, an intermediate layer that comprises chemical species that undergoes an endothermic reaction, and an outer layer that comprises an insulating layer.

BACKGROUND OF THE INVENTION

Warm temperatures often adversely affect blood samples that have been drawn from individuals. In poorer countries/communities, the lack of readily available refrigeration further exacerbates the situation. Not only do blood samples potentially degrade over time, but warm temperatures may alter and adversely affect the accuracy of blood test results.

A number of factors affect the accuracy of test results. Standard guidelines for blood sample handling state that plasma or serum should be separated (20-30 min) from cells as soon as possible after clot formation is complete to avoid clot-induced changes in the concentration of serum analyses. Many blood analyses deteriorate within a matter of hours in unseparated samples kept at ambient temperature. For most routine assays in a clinical laboratory, serum is the sample. The laboratory receives the specimen in the form of whole blood, and then separates the serum from the clot by centrifugation. For clinically useful and reliable test results, the interval between blood collection and serum separation must be controlled. Others have reported that some important analyses were significantly affected by temperature. For example, potassium, glucose, phosphate, creatinine, urea, ferritin, iron, lactate dehydrogenase, magnesium and calcium were not stable under storage conditions at higher temperatures. Others have reported that Serum gel or non-gel tubes might be used interchangeably for 11 analytes chilled or at 24° C., whereas some restrictions must be applied for glucose, AST, BUN, HDL, and uric acid. Still others have demonstrated that when stored at room temperature, only sodium, uric acid, bilirubin, cholesterol, triacylglycerols, aspartate aminotransferase, alanine aminotransferase, alkaline phosphatase, alpha-amylase and cholinesterase remained stable after 3 days. The data collected show that all quantities examined were sufficiently stable for four days in separated serum stored at +9 degrees C. Other researchers have shown that the stability of analytes separated from serum was less at higher temperature within 20 minutes of the clot relative to the analytes at 4±1 degree ° C. 48 hours after collection.

Accordingly, people have tried to ameliorate this bad situation by many possible means.

It would be advantageous to design a test tube that would lower the temperature of the contents allowing blood samples to remain stable longer in warmer climates. This would minimize dependency on refrigeration. The thought of a design for a test tube that would improve on the design commonly used by hospitals, clinics, research, and commercial laboratories all over the world would be revolutionary. The tube design would allow drawn blood samples to withstand these warmer climes.

BRIEF SUMMARY OF THE INVENTION

The present invention relates to a test tube that comprises at least three layers, an innermost first layer that is designed to hold a sample, an intermediate second layer that is designed to allow an endothermic chemical reaction to take place that lowers the temperature of not just the intermediate second layer but also the innermost first layer, and an outermost third layer that comprises insulation or insulating material.

In an embodiment, the innermost first layer is designed to hold blood. In an embodiment, the intermediate second layer is sealed so that additional chemicals in the chemical reaction cannot be added to the reaction. Alternatively, the intermediate second layer may be able to accommodate additional chemical reactants that can be added to the intermediate second layer. In an embodiment, there may be an extra layer that contains a vacuum between the intermediate second layer and the insulating outermost third layer. Alternatively, the insulating outermost layer might contain a vacuum.

In an embodiment, the chemical reactants in the intermediate second layer are kept separate from each other until they are needed (that is, until cooling or warming is desired). In an embodiment, there may be a plurality of compartments that contain the reactants (and keep them separate until needed). The compartments may be separated by a barrier, membrane and/or wall that can be fractured and/or broken to allow the reactants to contact each other reacting to generate the endothermic or exothermic reaction. In an embodiment, there are at least two compartments or at least four compartments. In a variation, there are four compartments. In a variation, half of the compartments contain water and half contain another chemical reactant that reacts with water to generate an endothermic or exothermic reaction. In a variation, the compartments may contain one or more vertical partitions or alternatively, the compartments may contain one or more horizontal partitions.

In an embodiment, the reactants may include sodium thiocyanate, sodium nitrate, ammonium chloride, ammonium thiocyanate, barium hydroxide, calcium chloride, thionyl chloride, cobalt (II) sulfate heptahydrate, and ethanoic acid with sodium.

The insulating outermost third layer may contain any material that is able to effectively insulate the intermediate second layer. Examples of insulating materials that may be used in the outermost third layer include silica aerogel, polyurethane, polyisocyanurate, a polyurethane spray foam, phenolic spray foam, Thinsulate, urea formaldehyde, urea foam, polystyrene, phenolic polymers, fiberglass, rice hulls, cellulose, cotton, icynene spray, cardboard, wool such as rock and slag wool batts, polyethylene foam, cementitious foam, perlite fill, wood chips, vermiculite, straw, papercrete, styrofoam, and mixtures thereof.

DETAILED DESCRIPTION OF THE INVENTION

The present invention relates to a two or three layer test tube that allows samples therein to remain at a colder temperature than would be ordinarily possible without the use of the two or three layer test tube. The two layer test tube contains the same layers as the three layer, with the understanding that the three layer test tube has one additional layer. The three layer tube comprises an interior layer (innermost first layer) that comprises the sample, an intermediate second layer that comprises chemical species that undergoes an endothermic reaction, and an outermost third layer that comprises an insulating layer comprising insulating materials. In an embodiment, the test tube may have additional layers, for example a fourth layer that is outside the third layer that may accommodate additional insulating materials.

Generally, sample as used herein refers to a biological product derived from plant or animal. Examples of a sample include blood samples, cell(s), tissue(s), organ(s), or other biological materials that one may desire to keep cold (or alternatively, to keep warm).

Thus, in an embodiment, the present invention relates to a three layer test tube that comprises an innermost first layer, an intermediate second layer that is capable of containing an endothermic chemical reaction, and an outermost third layer that comprises insulators and/or insulating materials.

In one embodiment, the three layer test tube may be able to accommodate an intermediate second layer where an exothermic reaction takes place. Thus, the three layer test tube in an embodiment may be suited for use as a test tube where material that needs to stay warm can be maintained.

In a variation, the intermediate second layer may be a closed system where additional chemical reactants cannot be added. Alternatively, the intermediate second layer may be an open system wherein additional chemical reactants can be added. By employing the latter open system, the time of cooling can be increased as additional reactant are added. Reactants would be added as needed to maintain the desired temperature.

In an embodiment, the three layer test tube may have a second intermediate layer wherein the chemical reactants that undergo the endothermic chemical reaction are kept separate from each other until the cooling (or warming for exothermic reactants) is needed. At such point, the chemical reactants can be brought into contact with each other allowing the endothermic chemical reaction to take place. In an alternate embodiment, the chemical reaction may be exothermic.

Results

Figure 1:
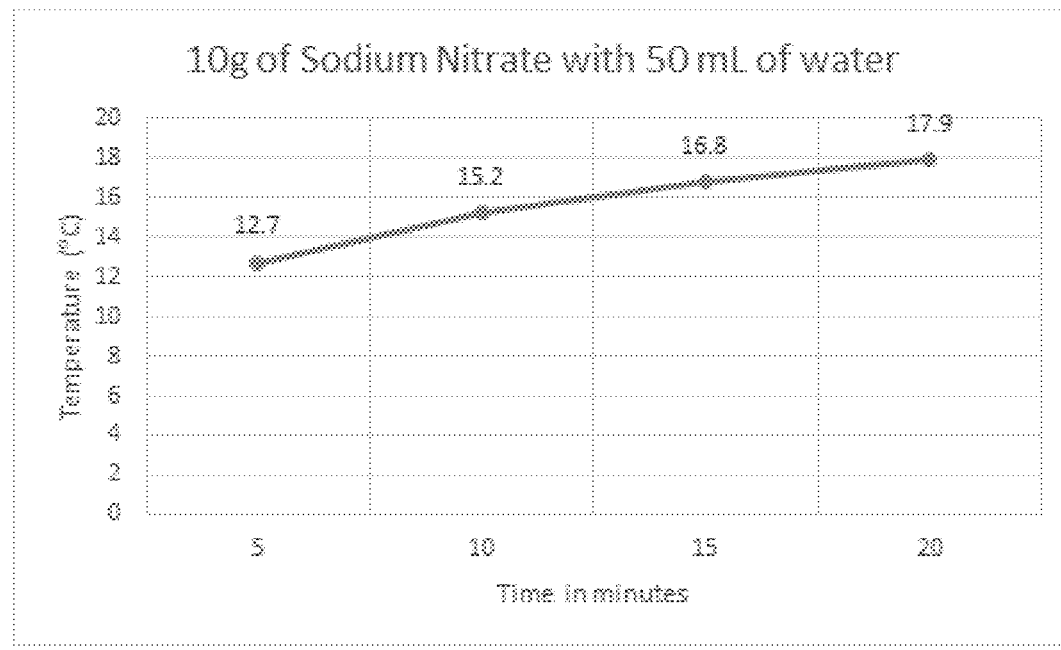
FIG. 1 shows a graph plotting the temperature of the reaction of sodium nitrate mixed with water over a 20 minute time period.
Figure 2:
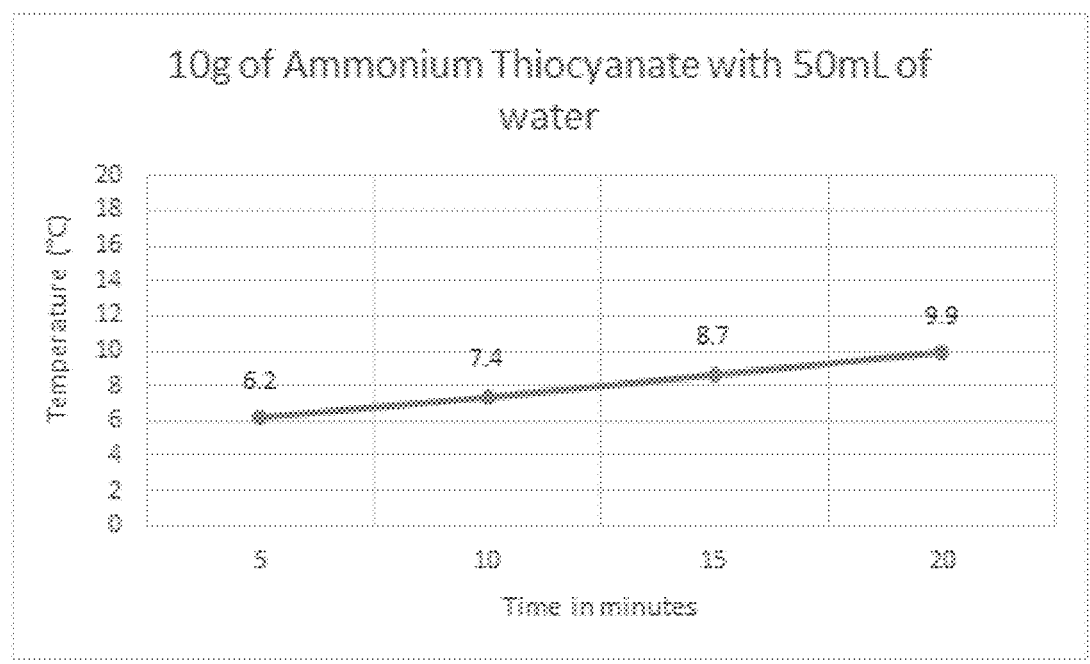
FIG. 2 shows a graph plotting the temperature of the reaction of ammonium thiocyanate mixed with water over a 20 minute time period.
Figure 3:
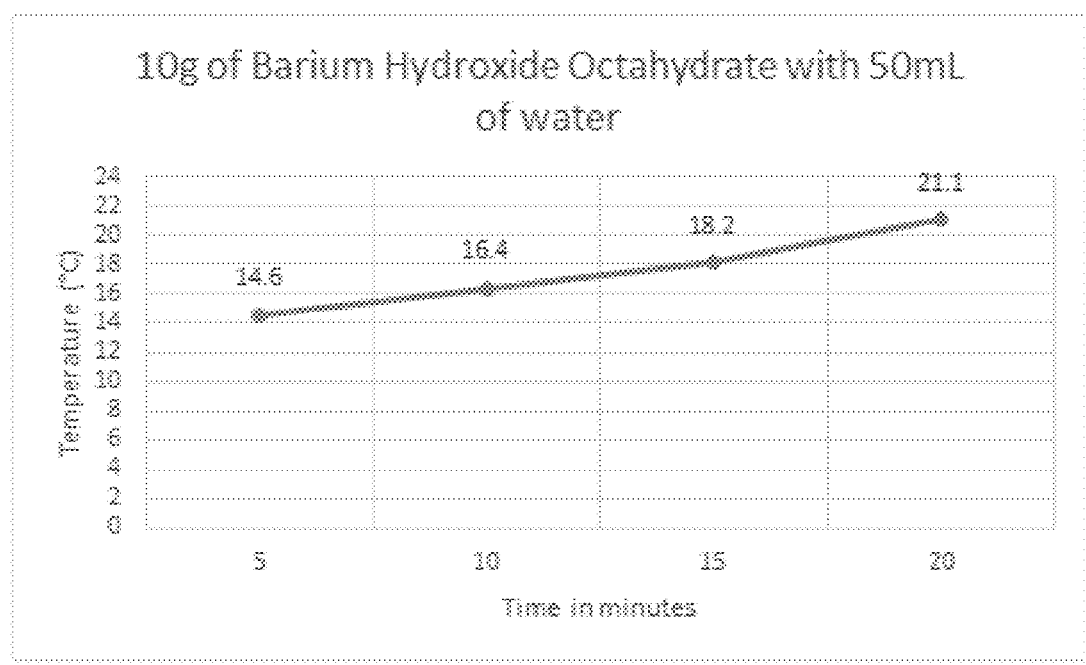
FIG. 3 shows a graph plotting the temperature of the reaction of barium hydroxide octahydrate mixed with water over a 20 minute time period.

Three different reactants were tested. In a first reaction, sodium nitrate was tested as shown in FIG. 1. In a second reaction, ammonium thiocyanate was tested as shown in FIG. 2. In a third reaction, barium hydroxide octahydrate was tested as shown in FIG. 3. Each reactant was tested under the same reaction conditions to test how much the temperature of the water would decrease over a period of time. The ideal goal temperature is 4° C. to 8° C. to keep the blood cool and adequate for accurate testing. The water's temperature before each reaction was started was 16.9° C.

The lowest initial temperature from all three reactants was the ammonium thiocyanate with a temperature of 6.2° C., an acceptable temperature for adequate storage of blood and testing.

Figure 4:
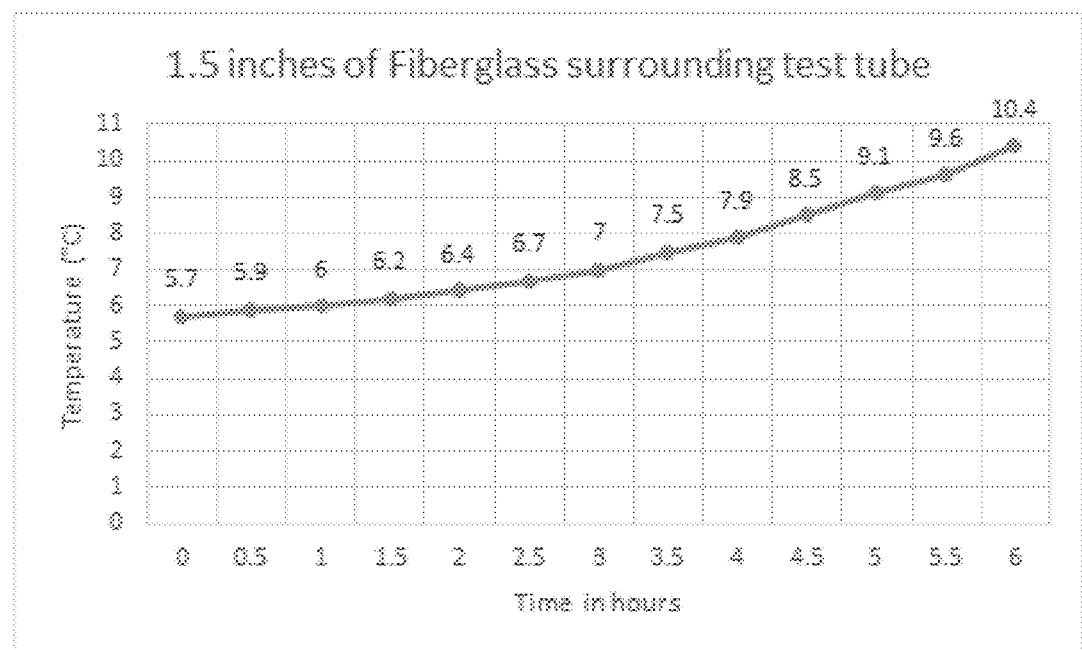
FIG. 4 shows a graph plotting the temperature of a simulated blood solution in the three layer test tube with fiberglass surrounding it as an insulator.
Figure 5:
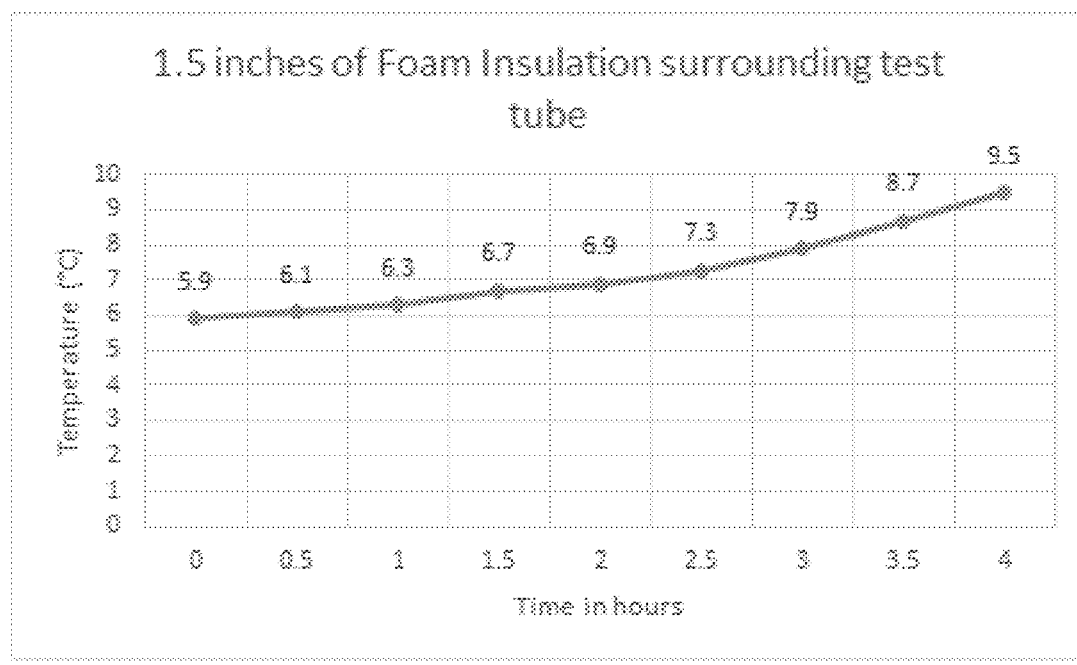
FIG. 5 shows a graph plotting the temperature of a simulated blood solution within the three layer test tube with foam insulation surrounding it as an insulator.
Figure 6:
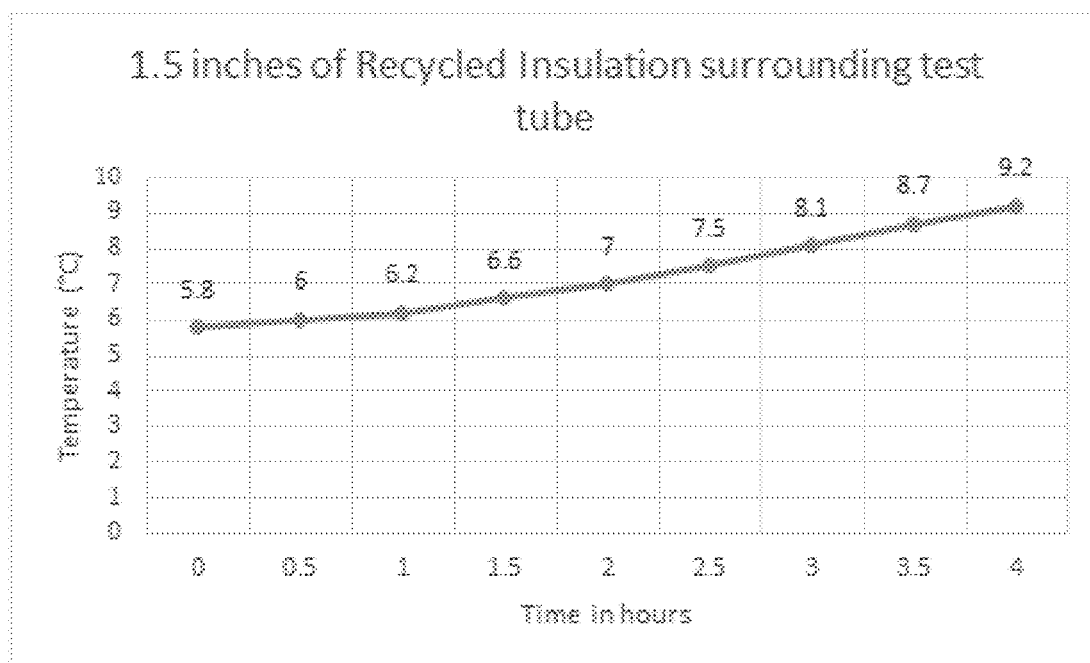
FIG. 6 shows a graph plotting the temperature of a simulated blood solution in the three layer test tube with recycled insulation surrounding it as an insulator.

Subsequently, three types of insulation were tested surrounding the test tube and endothermic reaction (ammonium thiocyanate) to see which insulation would stay cool the longest. The three types were fiberglass as shown in FIG. 4, foam as shown in FIG. 5, and recycled insulation as shown in FIG. 6. Each one was approached the same way by measuring the temperature of the simulated blood within the three layer test tube once the endothermic reaction had started. The temperature of the simulated blood was taken every 30 minutes until the simulated blood reached a temperature that was not considered as refrigeration.

The invention will now be explained with reference to the drawings. The drawings are not meant to limit the scope of the invention but are merely presented for illustrative purposes.

FIG. 1 shows a graph plotting the temperature of the reaction of sodium nitrate mixed with water over a 20 minute time period. The ambient air temperature was roughly 25° C. Three different reactants were tested. In a first reaction, sodium nitrate was tested as shown in FIG. 1. In a second reaction, ammonium thiocyanate was tested as shown in FIG. 2. In a third reaction, barium hydroxide octahydrate was tested as shown in FIG. 3. Each reactant was tested under the same reaction conditions to test how much the temperature of the water would decrease over a period of time. The ideal goal temperature is 4° C. to 8° C. to keep the blood cool and adequate for accurate testing. The water's temperature before each reaction was started was 16.9° C. Thus, the addition of 10 grams of sodium nitrate with 50 mls of water depresses the temperature to 12.7° C. and shows a gradual rise over 20 minutes to 17.9° C. At these depressed temperatures, a biological sample may maintain its integrity for longer periods of time than would be attained by having the blood sample exposed to ambient air.

FIG. 2 shows a graph plotting the temperature of the reaction of ammonium thiocyanate mixed with water over a 20 minute time period. The addition of 10 grams of ammonium thiocyanate with 50 mls of water depresses the temperature to 6.2° C. and shows a gradual rise over 20 minutes to 9.9° C.

FIG. 3 shows a graph plotting the temperature of the reaction of barium hydroxide octahydrate mixed with water over a 20 minute time period. The addition of 10 grams of barium hydroxide octahydrate with 50 mls of water depresses the temperature to 14.6° C. and shows a gradual rise over 20 minutes to 21° C.

FIG. 4 shows a graph plotting the temperature of a simulated blood solution in the three layer test tube with fiberglass surrounding it as an insulator. The temperature was depressed using ammonium thiocyanate and water and the temperature of the simulated blood solution was tested over a 6 hour period. The temperature started at time 0 at a temperature of 5.7° C. and gradually rose to a temperature of 10.4° C. over a period of 6 hours. Interestingly, the temperature at 5.5 hours was 9.6° C., which was still below the temperature after 20 minutes without any insulation of 9.9° C. (see FIG. 2).

FIG. 5 shows a graph plotting the temperature of a simulated blood solution within the three layer test tube with foam insulation surrounding it as an insulator. The temperature was depressed using ammonium thiocyanate and water and the temperature of the simulated blood solution was tested over a 4 hour period. The temperature started at time 0 at a temperature of 5.9° C. and gradually rose to a temperature of 9.5° C. over a period of 4 hours. Interestingly, the temperature at 4 hours was 9.5° C., which was still below the temperature after 20 minutes without any insulation of 9.9° C. (see FIG. 2).

FIG. 6 shows a graph plotting the temperature of a simulated blood solution in the three layer test tube with recycled insulation surrounding it as an insulator. The temperature was depressed using ammonium thiocyanate and water and the temperature of the simulated blood solution was tested over a 4 hour period. The temperature started at time 0 at a temperature of 5.8° C. and gradually rose to a temperature of 9.2° C. over a period of 4 hours. Interestingly, the temperature at 4 hours was 9.2° C., which was still below the temperature after 20 minutes without any insulation of 9.9° C. (see FIG. 2).

Figure 7:
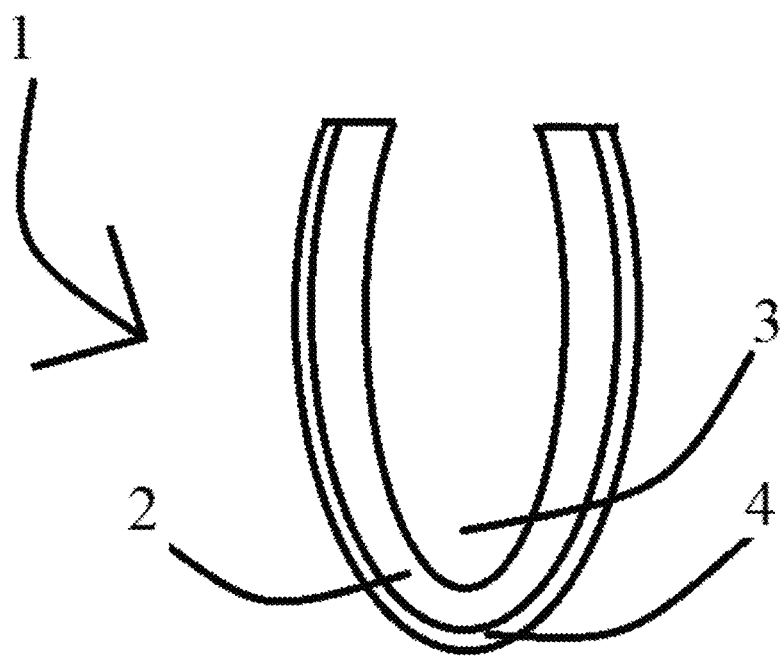
FIG. 7 shows an embodiment of the three layer test tube of the present invention.

FIG. 7 shows a cross sectional view of one embodiment of the three layer test tube 1. The innermost section 3 is designed to hold the biological sample that is to be cooled or heated. Intermediate layer 2 is the layer where the endothermic or exothermic reaction takes place and outer layer 4 contains insulating material as discussed herein. Although not shown, it should be understood that innermost section 3 may contain a stopper that allows the innermost section 3 to contain a vacuum that allows one to assist in the siphoning of blood or some other biological sample into the innermost section 3.

Figure 8:
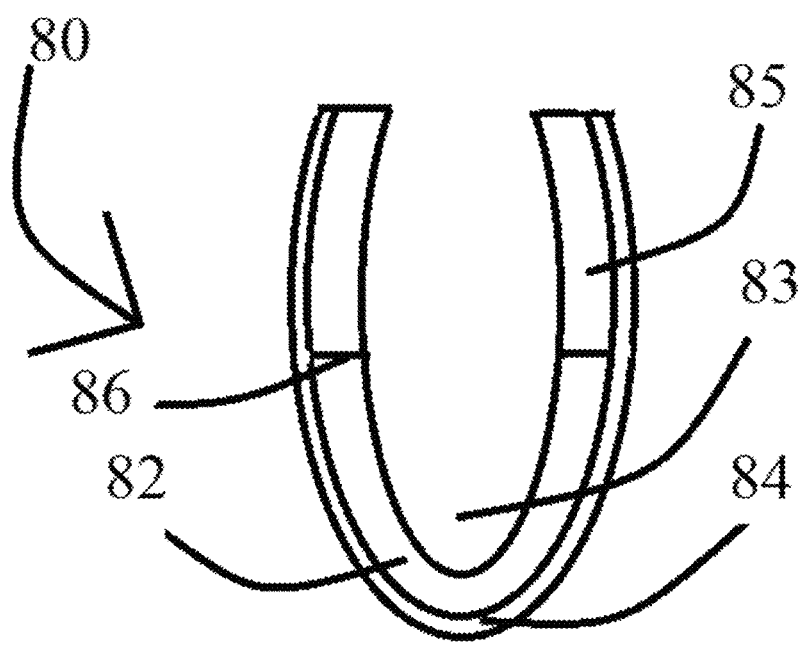
FIG. 8 shows an embodiment of the three layer test tube of the present invention with a horizontal partition that separates the reactants that when joined together react endothermically.

FIG. 8 shows another embodiment of the three layer test tube 80. In this figure, the innermost section 83 is designed to hold the biological sample that is to be cooled or heated. The reactants that are to undergo reaction to generate either an endothermic or exothermic reaction are initially kept apart by having a first reactant in upper intermediate layer 85 and the second reactant in the lower intermediate layer 82. Partition 86 is what separates upper intermediate layer 85 from lower intermediate layer 82. Partition 86 can be made from any of a plurality of substances including a substance that is labile to light. Accordingly, when the three layer test tube has been irradiated with light (either of a particular wavelength or by, for example, sun light), the partition ruptures allowing the reactants in upper intermediate layer 85 (containing the first reactant) and lower intermediate layer 82 (containing the second reactant) to react with each other thereby generating the endothermic or exothermic reaction. Outer layer 84 is an insulating layer that may contain the insulating material described herein. As discussed previously outer layer 84 may alternatively possess a vacuum. Alternatively, partition 86 may be made of a material that upon shaking the three part test tube 80 ruptures, allowing the reactants in upper intermediate layer 85 (containing the first reactant) and lower intermediate layer 82 (containing the second reactant) to react with each other thereby generating the endothermic or exothermic reaction. Although the partition 86 is shown as a horizontal partition, it should be understood that the partition may be oriented vertically.

Figure 9:
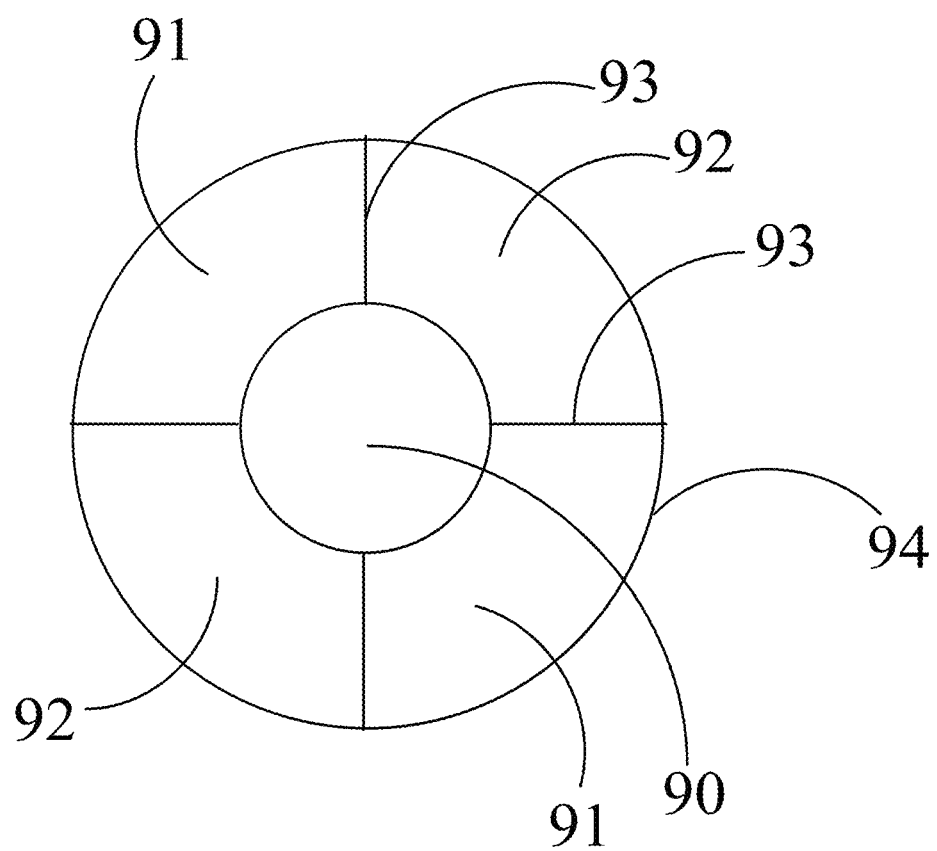
FIG. 9 shows a top down cross sectional view of an embodiment of the three layer test tube with vertical partitions.

FIG. 9 shows a top down cross sectional area of another embodiment of a three layer test tube device. In this embodiment, a test tube is placed in central hole 90. Upon placing the test tube in central hole 90, the partition 93 breaks that exists between first and third compartments 91 and second and fourth compartments 92 allowing the first reactant that is present in first and third compartments 91 to react with the second reactant that is present in second and fourth compartments 92, thereby generating either an endothermic or exothermic reaction. This reaction keeps the test tube that has been placed in central hole 90 cool (or under exothermic conditions keeps the test tube warm). Although the outermost layer 94 is not shown with much thickness, it should be understood that the outermost layer, which contains an insulator can be whatever thickness that is desired to prolong the reaction at the temperature of the reaction. The outermost layer 94 of the three layer test tube may contain any of the insulating materials that are described herein.

Figure 10:
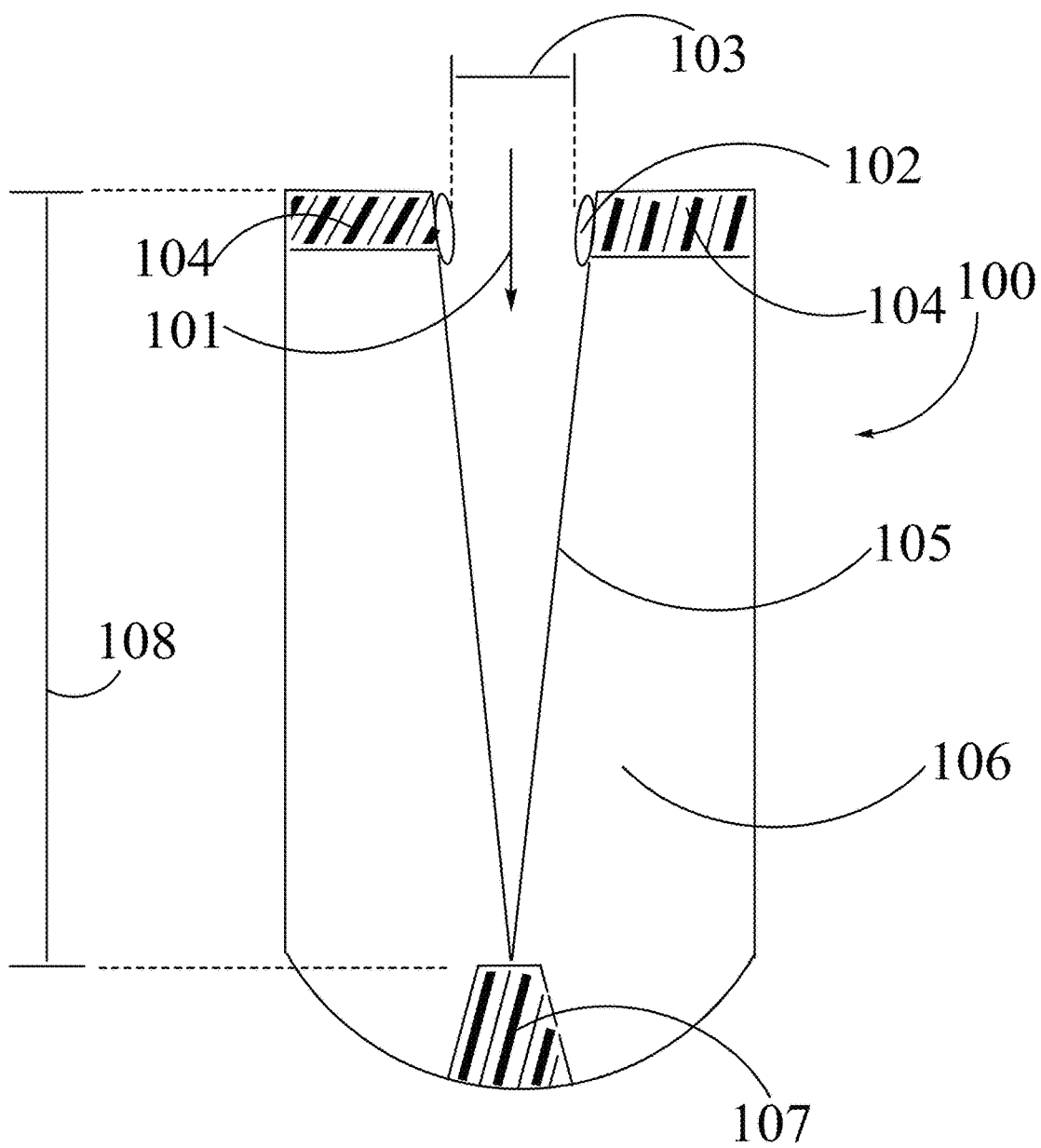
FIG. 10 shows a side cross sectional view of an embodiment of a two layer test tube device.

FIG. 10 shows a cross sectional view of the length of the two layer test tube 100. This cross sectional view of the length corresponds to a similar embodiment of the invention as shown in the top down cross sectional view of the three layer test tube as shown in FIG. 9 except that the outermost layer is not present. The test tube that contains the biological sample is inserted into the two layer test tube 100 in the direction shown by arrow 101. By insertion of the test tube, partition 105 is broken, thus allowing the first reactant and the second reactant that are in the various compartments 106 and 112 (see FIG. 12) to mix. The partition 105 is of a shape so that when the test tube is inserted it is able to enter between rubber guards 102 and as it proceeds down the length 108 of the two layer test tube, the partition 105 creates a conical shape that as the test tube approaches rubber stopper 107 it becomes narrower. At a point, the inner conical shape created by partition 105 is not able to withstand the pressure caused by the entering test tube and the partition 105 breaks, thus allowing the first reactant and the second reactant that are in the various compartments 106 and 112 (see FIG. 12) to mix.

Accordingly, partition 105 should be made of a material that is sufficiently sturdy so that it does not break upon transport of the three layer test tube but does break when a test tube is inserted into the device. For example, it is contemplated that a thin glass (for example, the thickness may be the thickness of a microscope slide or cover slip) or a breakable plastic can be used as materials for partition 105. In an embodiment, if glass is to be used as the material for partition 105, the glass may be on the order of 0.13 to 0.17 mm in thickness. In an embodiment, if the partition 105 is a breakable plastic, it may be Acrylic such as Plexiglas or Acrylite, which is relatively fragile, i.e., it has low impact strength or toughness. Other plastics that may be used include basic polystyrene, which also has the property of being a low impact strength plastic.

It should be noted that in the embodiment that is shown, the rubber stopper 107 at the bottom of the three layer test tube is designed to stop the test tube. Accordingly, the length 108 from the top of the two layer device to the top of stopper 107 is roughly the same length as the length of a test tube that is inserted into the two layer device. The purpose of rubber stopper 107 is to stop the test tube from going further than it should, preventing the reactants from potentially entering the test tube. The diameter of the test tube is roughly the same diameter of the opening diameter 103 wherein the test tube is inserted. Also, at the top of the two layer device are rubber lid 104, which have rubber bumper 102 adjacent to rubber lid 104. The rubber bumper 102 may be made of a single rubber bumper that circumnavigates the entire opening circumference or alternatively, the rubber bumper 102 may comprise one or more rubber bumpers that circumnavigate only a portion of the opening circumference.

Figure 11:
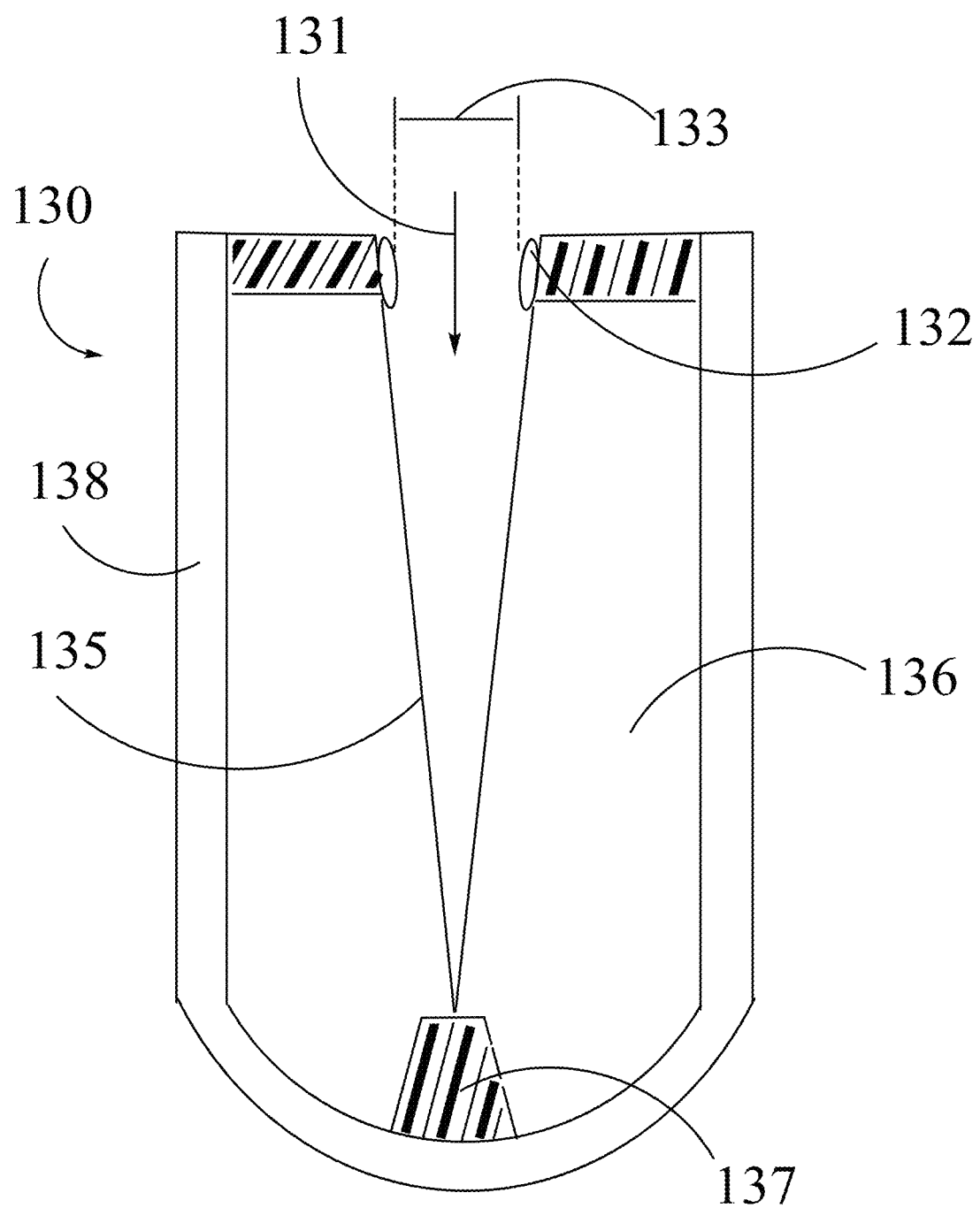
FIG. 11 shows a side cross sectional view of an embodiment of a three layer test tube device.
Figure 12:
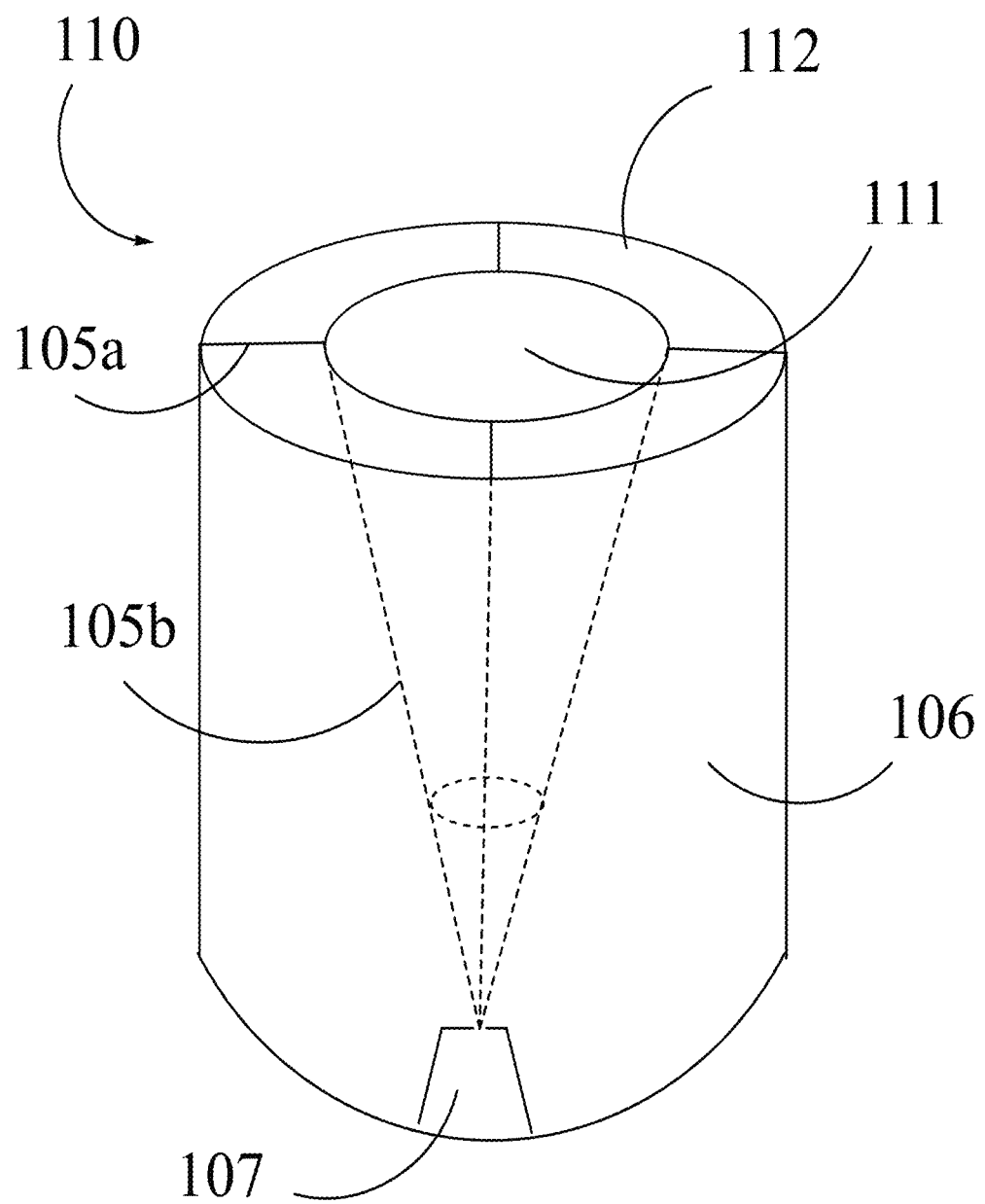
FIG. 12 shows a perspective view of a two layer test tube device.

It should be noted that the embodiment shown in FIG. 10 is really only two layers—the innermost test tube and the middle layer where a first reactant mixes with a second reactant in compartments 106 and 112 (see FIG. 12). The device lacks an outermost layer that might contain insulating material and/or alternatively might contain a vacuum. This outermost layer has been discussed at length with respect to other figures/embodiments and is actually shown in FIG. 11.

FIG. 11 shows a similar embodiment to the embodiment of FIG. 10 except that an additional insulating outermost layer 138 is present. As described above, this device 130 comprises an insulating layer that may contain the insulating materials discussed at length herein or alternatively, might contain a vacuum that in effect also insulates the middle layer 136. Similar to FIG. 10, when a test tube is inserted in the direction of arrow 131 into opening 133, partition 135 is broken, allowing the reactants that are present in middle layer 136 to mix thus generating an exothermic or endothermic reaction. Rubber guards 132 prevent the inserted test tube from going too far as does the rubber stopper 137 present at the bottom of the device that are designed to serve as a bumper for the bottom of the test tube.

FIG. 12 shows a perspective view of an alternative two layer device 110 that is a slight modification from other embodiments shown herein. Top portion of partition 105a and internal portion of partition 105b make up portions of the partition 105 that separates the compartments of the two layer test tube. Partition 105 is broken when a regular test tube is inserted into the opening 111 of the two layer device. It should be noted that the conical shape of the partition means that as the test tube is inserted, the internal portion of partition 105b will break. The breaking of the internal portion of partition 105b results in the reactants that are present in compartments 106 and 112 mixing, thereby generating an endothermic or exothermic reaction. In one embodiment, the reaction is endothermic. In another, the reaction is exothermic. The material that may be used as partition material includes thin glass (such as glass that is of a thickness comparable to a cover slip for a microscope slide). The pressure from the insertion of the test tube Rubber stopper 107 is shown that prevents the inserted test tube from going too far down into the two layer device. Although not shown in FIG. 12, it should be understood that rubber guards 102 or rubber lids 104 (as shown in FIG. 10) may be present at the circumference of opening 111 so as to provide friction for an inserted test tube into opening 111 so as to prevent it from going too deep into the two layer device 110.

Figure 13:
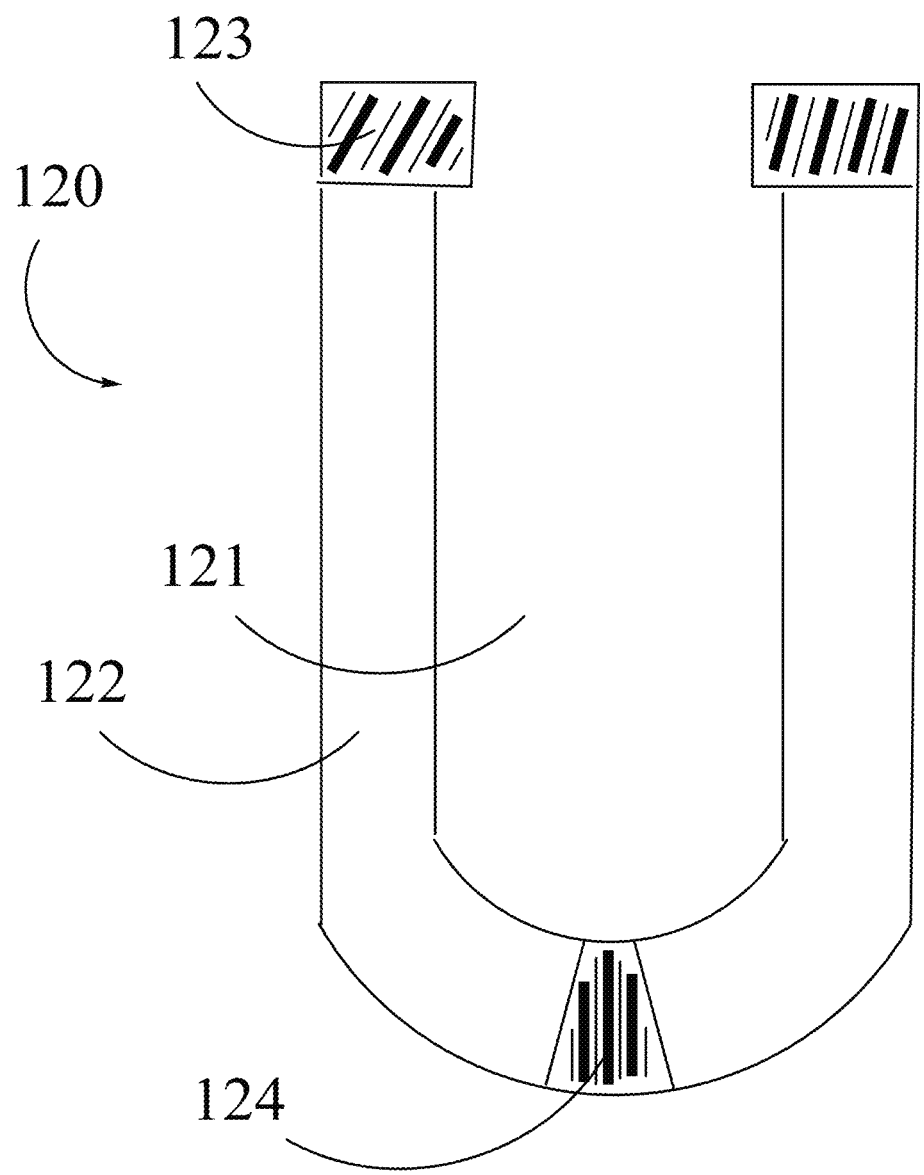
FIG. 13 shows a two layer device that is designed to accommodate another two layer device.

FIG. 13 shows another embodiment of the invention. In this embodiment a two layer device 120 is shown that comprises an innermost layer 121 that is designed to accommodate a test tube that has been inserted into the innermost layer. The inserted test tube may be a one layer test tube or alternatively, it may be a two layer test tube that has an innermost layer that has a sample in it and a middle layer that has reactants in it (see for example, the two layer test tube of FIG. 12). The reactants generate either an endothermic or exothermic reaction as discussed herein. In FIG. 13, the outermost layer 122 is designed to have insulation in it. Thus, by combining the two layer test tube device 110 of FIG. 12 with the two layer device 120 of FIG. 13, one is left with a three layer test tube (note that it is not a four layer device because the innermost layer of FIG. 13 is replaced by the middle layer that is shown in FIG. 12). That is, one has an innermost layer that comprises the sample (from the test tube of FIG. 12), a middle layer that comprises reactants that have an endothermic or exothermic reaction (from the test tube device of FIG. 12), and an outermost layer that comprises insulation (from the test tube device 120 as shown in FIG. 13). The two layer device of FIG. 13 also has one or more rubber stoppers 123 that is/are designed to accommodate the inserted two layer device 110 of FIG. 12 or a test tube (e.g., to provide friction that holds the test tube in place). The one or more rubber stoppers 123 are designed to provide friction to the outside of the inserted test tube thereby providing a tight seal when it is inserted into the two layer device 120 as shown in FIG. 13. If there is a single rubber stopper 123, it may circumnavigate the circumference of the two layer device 120 of FIG. 13, thereby providing friction and a tight seal for the entire circumference of the two layer device 120 of FIG. 13. There is also a bottom stopper 124 that may be comprised of rubber that is designed to stabilize and provide support for the inserted test tube.

Thus, in an embodiment, the present invention relates to either a two or three layer device that can be used to keep a sample cold. Alternatively, it is contemplated that the two or three layer device may warm a sample that is inserted into it. In general, the two layer device comprises an innermost layer that contains the sample and an intermediate layer that comprises reactants that generate an endothermic (or alternatively, an exothermic) reaction. In general, the three layer device comprises the same two layers that the two layer device comprises with an additional outer layer that comprises an insulating layer as discussed herein.

There are several variations to the design of the two or three layer devices that should be apparent from the figures. These variations include a one, a two, or a three device variation.

In the three device variation, a regular test tube may be inserted into a two layer device that breaks partitions (see FIG. 12) allowing reactants in compartments to react to generate either an endothermic or exothermic reaction (depending on the reactants therein). The two layer device may be inserted into another two layer device (see FIG. 13) that comprises an interior layer that allow the insertion of another two layer device (for example, the two layer device of FIG. 12) and an outer layer that comprises an insulating layer comprising the insulation as disclosed herein. It should be noted that the two layer device as shown in FIG. 13 can be reused as it does not contain any features that are broken.

The two device variation may be a test tube that is inserted into a two layer device (for example FIG. 12) that may lack the outermost insulating layer or alternatively, it may be a test tube that can be inserted into a three layer device that comprises the sample (in the test tube), the interior layer of the three layer device that is designed to accommodate the test tube, a middle layer that comprises compartments with the reactants that are designed to mix to give an endothermic (or exothermic reaction), and an outermost layer that comprises an insulating layer.

The one device variation is a self-contained variation that comprises either two or three layers. The one device variation that comprises two layers comprises an innermost layer that is designed to hold the sample and a middle layer that optionally comprises compartments designed to hold reactants that will react when mixed to give an endothermic (or alternative, an exothermic) reaction. In one variation, the innermost layer may also contain a vacuum that allows one to suction blood into the innermost layer (it should be noted that the innermost layer in this case would be sealed). The one device variation that comprises three layers comprises the same two layers as the one device variation that comprises two layers and it additionally comprises an outermost layer that comprises an insulating layer.

Thus, in an embodiment, the invention relates to a two layer device comprising an innermost layer and a middle layer, the innermost layer designed to hold a test tube containing a sample, and the middle layer comprising at least two compartments, at least a first compartment and a second compartment, the first compartment and the second compartment designed to accommodate a first reactant and a second reactant, respectively.

In an embodiment, the device is a test tube, which comprises either two or three layers. If the test tube is two layers, it comprises an innermost layer and a middle layer, and if the test tube is three layers, it comprises an innermost layer, a middle layer, and an outermost layer. The innermost layer is designed to hold the sample, the middle layer is designed to allow a reaction to occur between reactants thereby generating an endothermic or an exothermic reaction. The outermost layer is designed to be an insulating layer that comprises insulating material.

In one variation, in the two layer device there exists at least one partition situated between the first compartment and second compartment, the at least one partition designed to break when pressure is exerted on the at least one partition allowing the first reactant and second reactant to mix and react. In a variation, the at least one partition is made of thin glass or breakable plastic.

In an embodiment, when the first reactant and the second reactant react endothermically. In a variation, when the first reactant and the second reactant react, they react exothermically.

In an embodiment, the first reactant is water.

In an embodiment, the second reactant comprises one or more of sodium thiocyanate, sodium nitrate, ammonium chloride, ammonium thiocyanate, barium hydroxide, calcium chloride, thionyl chloride, cobalt (II) sulfate heptahydrate, or ethanoic acid with sodium.

In an embodiment, the pressure that breaks the partition is caused by insertion of a test tube into the two layer device. In a variation, the partition comprises glass. In a variation, the glass is of a thickness that is between about 0.13 and 0.17 mm in thickness.

In one variation, the two layer device further comprises an outermost layer. Thus, in this variation, the device is a three layer device comprising an innermost layer, a middle layer, and an outermost layer. In a variation, the outermost layer comprises insulation.

In an embodiment, the insulation that comprises the outermost layer is one or more members selected from the group consisting of silica aerogel, polyurethane, polyisocyanurate, a polyurethane spray foam, phenolic spray foam, thinsulate, urea formaldehyde, urea foam, polystyrene, phenolic polymers, fiberglass, rice hulls, cellulose, cotton, icynene spray, cardboard, wool such as rock and slag wool batts, polyethylene foam, cementitious foam, perlite fill, wood panels, vermiculite, straw, papercrete, Styrofoam, and mixtures thereof.

In a variation, the two layer device comprises additional compartments. There may be, for example, 3, 4, 5, 6, 7, 8, 9, or 10 compartments or more. In a variation, there exist four compartments, two compartments that contain the first reactant and two compartments that contain the second reactant.

In an embodiment, the present invention relates to a method of keeping a sample at an elevated or lower temperature, the method comprising inserting the sample into a two layer device comprising an innermost layer and a middle layer, the innermost layer comprising a test tube containing the sample, and the middle layer comprising at least two compartments, a first compartment and a second compartment, the first compartment and the second compartment designed to accommodate a first reactant and a second reactant, and the first compartment and the second compartment being separated by a partition, breaking the partition by exertion of a force thereby allowing said first reactant and second reactant to mix whereby when the first reactant and second reactant mix, an exothermic or endothermic reaction is created.

In a variation, the method of the invention comprises a first reactant that comprises water. In a variation of the method, the second reactant comprises one or more of sodium thiocyanate, sodium nitrate, ammonium chloride, ammonium thiocyanate, barium hydroxide, calcium chloride, thionyl chloride, cobalt (II) sulfate heptahydrate, or ethanoic acid with sodium.

In one variation of the method, the partition comprises thin glass or breakable plastic, In one variation of the method, the pressure is exerted by insertion of a test tube into the two layer device.

In one variation of the method, the reaction is endothermic. In a variation of the method, the reaction is exothermic.

In one variation, the two layer device further comprises an outermost insulating layer. IN one variation, the outermost layer comprises the insulating materials discussed herein. In one variation, the temperature of the sample stays below about 11° C. for at least about 5.5 to 6 hours. In one variation, the temperature of the sample stays below about 10.5° C. for at least about 5.5 hours.

It is contemplated and therefore within the scope of the invention that any feature that is discussed above can be combined with any other feature to make the devices, apparatuses, systems, and methods of the present invention, even if they are not discussed together. In any event, the invention is defined by the below claims. It should be apparent that minor modifications can be made to the present invention without departing from the spirit and scope of the invention.

The following references are incorporated by reference in their entireties.

"All About Blood." Red on Tap. Genensis Framework, 9 May 2011. Web. 20 Nov. 2015 Cuhadar, Serap, Ayşenur Atay, Mehmet Koseoglu, Ahmet Dirican, and Aysel Hur. "Stability Studies of Common Biochemical Analytes in Serum Separator Tubes with or without Gel Barrier Subjected to Various Storage Conditions." *Biochemia Medica*. Croatian Society of Medical Biochemistry and Laboratory Medicine. Web. 11 Dec. 2015.

"LabNotes—Volume 14." *Managing Preanalytical Variability in Hematology*. Becton, Dickinson and Company. 2014 BD, 10 Nov. 2004. Web. 30 Nov. 2015

"Result Filters." *National Center for Biotechnology Information*. U.S. National Library of Medicine. Web. 11 Dec. 2015.

Trulock, E. P., and Iii. *Arterial Blood Gases*. U.S National Library of Medicine, 17 Jan. 1990. Web. 30 Nov. 2015

I claim:

1. A two layer device comprising: an innermost layer and a middle layer, the innermost layer designed to hold a test tube containing a sample or a sample directly, and the middle layer comprising at least two compartments, at least a first compartment and a second compartment, the first compartment and the second compartment designed to accommodate a first reactant and a second reactant, respectively, the device further comprising a rubber guard, rubber stopper, and/or rubber bumper to prevent an inserted test tube from going too far into the device.

2. The two layer device of claim 1, wherein the first compartment and the second compartment comprise at least one partition that exists between the first compartment and second compartment, the at least one partition designed to break when pressure is exerted on the at least one partition allowing the first reactant and second reactant to mix and react.

3. The two layer device of claim 2, wherein the at least one partition is made of thin glass or breakable plastic.

4. The two layer device of claim 2, wherein when the first reactant and the second reactant react endothermically.

5. The two layer device of claim 4, wherein the first reactant is water.

6. The two layer device of claim 4, wherein the second reactant is a member selected from the group consisting of sodium thiocyanate, sodium nitrate, ammonium chloride, ammonium thiocyanate, barium hydroxide, calcium chloride, thionyl chloride, cobalt (II) sulfate heptahydrate, and ethanoic acid with sodium.

7. The two layer device of claim 2, wherein the pressure is exerted by insertion of a test tube into the two layer device.

8. The two layer device of claim 3, wherein the partition comprises glass.

9. The two layer device of claim 8, wherein the glass is of a thickness that is between 0.13 and 0.17 mm in thickness.

10. The two layer device of claim 1, further comprising an outermost layer.

11. The two layer device of claim 10, wherein the outermost layer comprises insulation.

12. The two layer device of claim 11, wherein the insulation is one or more members selected from the group consisting of silica aerogel, polyurethane, polyisocyanurate, a polyurethane spray foam, phenolic spray foam, urea formaldehyde, urea foam, polystyrene, phenolic polymers, fiberglass, rice hulls, cellulose, cotton, icynene spray, cardboard, wool such as rock and slag wool batts, polyethylene foam, cementitious foam, perlite fill, wood chips, vermiculite, straw, papercrete, and mixtures thereof.

13. The two layer device of claim 2, further comprising additional compartments.

14. A method of keeping a sample at an elevated or lower temperature, said method comprising:
inserting the sample into a two layer device comprising an innermost layer and a middle layer, the innermost layer comprising a test tube containing the sample, and the middle layer comprising at least two compartments, a first compartment and a second compartment, the first compartment and the second compartment designed to accommodate a first reactant and a second reactant, and the first compartment and the second compartment being separated by a partition, breaking the partition by exertion of a force thereby allowing said first reactant and second reactant to mix whereby when the first reactant and second reactant mix, an exothermic or endothermic reaction is created.

15. The method of claim 14, wherein the first reactant comprises water.

16. The method of claim 14, wherein the second reactant comprises one or more of sodium thiocyanate, sodium nitrate, ammonium chloride, ammonium thiocyanate, barium hydroxide, calcium chloride, thionyl chloride, cobalt (II) sulfate heptahydrate, or ethanoic acid with sodium.

17. The method of claim 14, wherein the partition comprises thin glass or breakable plastic.

18. The method of claim 14, wherein pressure is exerted by insertion of a test tube into the two layer device.

19. The method of claim 14, wherein the reaction is endothermic.

20. The method of claim 19, further comprising an outermost insulating layer, wherein the temperature stays below 11° C. for at least 5.5 hours.

21. A three layer device comprising: an innermost layer designed to accommodate a sample, a middle layer designed to accommodate reactants that generate an exothermic or endothermic reaction, and an outermost layer that comprises insulating material.

22. The three layer device of claim 21, wherein the sample comprises blood.

* * * * *